United States Patent [19]
Mount et al.

[11] Patent Number: 5,618,495
[45] Date of Patent: Apr. 8, 1997

[54] COLORIMETRIC TITRATION METHOD AND APPARATUS

[76] Inventors: Andrew S. Mount, 1024 Old Stone Church Rd., No. 414, Clemson, S.C. 29631; Douglas Paul, 418 Rockingham Rd., Seneca, S.C. 29678; Alfred P. Wheeler, 201 Augusta Rd., Clemson, S.C. 29631

[21] Appl. No.: 417,447

[22] Filed: Apr. 5, 1995

Related U.S. Application Data

[63] Continuation of Ser. No. 97,780, Jul. 26, 1993, abandoned.
[51] Int. Cl.$^6$ .................................................. G01N 21/25
[52] U.S. Cl. ...................... 422/82.05; 422/75; 422/76; 422/77; 422/108; 436/51; 436/163; 356/217; 356/226; 356/436
[58] Field of Search ...................... 436/163, 51; 422/55, 422/62, 68.1, 75–77, 82.05, 82.08, 108; 356/337, 338, 343, 432, 434, 436, 217, 222, 226

[56] References Cited

U.S. PATENT DOCUMENTS

| | | | |
|---|---|---|---|
| 3,026,182 | 3/1962 | Janowski et al. | 23/230 |
| 3,481,707 | 12/1969 | Brodkorb et al. | 23/253 |
| 3,723,062 | 3/1973 | Dahms | 436/51 |
| 3,725,658 | 4/1973 | Stanley et al. | 250/71 R |
| 3,730,685 | 5/1973 | Prohaska | 23/230 R |
| 3,748,044 | 7/1973 | Liston | 356/180 |
| 3,769,178 | 10/1973 | Rothermel, Jr. | 436/51 |
| 3,941,487 | 3/1976 | Ehret et al. | 356/181 |
| 4,018,565 | 4/1977 | Fletcher, III et al. | 436/51 |
| 4,063,817 | 12/1977 | Shimamura et al. | 356/93 |
| 4,092,121 | 5/1978 | Rutishauser et al. | 23/253 R |

(List continued on next page.)

OTHER PUBLICATIONS

A. Mount, Laser Detection System Disclosure to Clemson University, pp. 1–6, 1992.
Franson, ed. "Standard Methods For the Examination of Water and Waste Water," 441–448, Feb. 1992.
Brinkman Dipping Probe Colorimeter Product Literature, 1992.

(List continued on next page.)

*Primary Examiner*—James C. Housel
*Assistant Examiner*—Rachel Heather Freed
*Attorney, Agent, or Firm*—Troutman Sanders LLP; Joel S. Goldman, Esq.

[57] ABSTRACT

The invention relates to colorimetric titration method, a titrator and colorimeter device. The titrating apparatus comprises radiant energy means for producing radiant energy. The device includes means for modulating an amplitude of an intensity of the radiant energy at a modulation frequency. The radiant energy is partially absorbed by an adjacent solution within a sample beaker having a color indicator dissolved therein. Radiant energy focusing means focuses the modulated radiant energy transmitted through the sample and beaker on radiant energy detection means. The radiant energy detection means produces a transmitted signal wherein an intensity of the transmitted signal is directly proportional to the intensity of transmitted energy. Filtering means filters the transmitted signal, such that a center frequency of the filtering means matches the modulation frequency of the radiant energy means. The filtering means produces filtered transmitted energy signal representative of only the amount radiant energy transmitted through the solution from the radiant energy source, free of other sources of radiant energy. The colorimetric titrator also includes means for constructing a titration curve, means for computing the first derivative of the titration curve, means for computing the second derivative of the titration curve, control means for controlling titrant addition means in response to the first derivative of the titration curve and means for calling the endpoint of the titration by using the second derivative of the titration curve.

24 Claims, 10 Drawing Sheets

U.S. PATENT DOCUMENTS

| | | | |
|---|---|---|---|
| 4,095,272 | 6/1978 | Janzen | 364/497 |
| 4,283,201 | 8/1981 | DeFord et al. | 23/230 A |
| 4,302,299 | 11/1981 | Ishikawa | 204/1 T |
| 4,324,556 | 4/1982 | Robertson et al. | 23/230 B |
| 4,457,893 | 7/1984 | Takekawa | 422/64 |
| 4,749,552 | 6/1988 | Sakisako et al. | 422/75 |
| 4,907,878 | 3/1990 | Arditty et al. | 356/128 |
| 4,917,495 | 4/1990 | Steenhoek | 356/328 |
| 4,949,400 | 8/1990 | Leveen | 356/420 |
| 4,950,610 | 8/1990 | Tittle | 436/163 |
| 4,994,396 | 2/1991 | Lefkowitz et al. | 436/136 |
| 5,030,419 | 7/1991 | Ellis et al. | 422/82.09 |
| 5,073,029 | 12/1991 | Eberly et al. | 356/432 |
| 5,104,527 | 4/1992 | Clinkenbeard | 210/94 |
| 5,125,747 | 6/1992 | Sayegh et al. | 356/407 |
| 5,181,082 | 1/1993 | Jeannotte et al. | 356/436 |

OTHER PUBLICATIONS

"Instrumental Methods of Analysis", Sixth Ed., Chap. 3, pp. 83–86.

A. Mount, Laser Detection System Disclosure to Clemson University, 1992.

Brochure of PULNiX America, Inc., entitled "Seeka Brand CS–C3 Color Sensor" received on Aug. 13, 1994.

FIG. 11

COLORIMETRIC TITRATION METHOD AND APPARATUS

This is a continuation of application Ser. No. 08/097,780, filed on Jul. 26, 1993 and now abandoned.

BACKGROUND OF THE INVENTION

Titrations are done to determine the strength of a solution or the concentration of an unknown substance in a solution. Therefore, titrations are analytical procedures that are based on many different chemical reactions that are of interest to the analytical chemist.

A titration may be performed if the chemistry of the desired reaction meets three criteria: the reaction is fast, the reaction proceeds stoichiometrically, and the change in free energy is reasonably large. If these criteria are satisfied then it is possible to determine the endpoint of a reaction by color change of an indicator, by potentiometric means via electrode, by conductivity measurement, by thermal measurement (quantity of heat evolved), and by other means as well.

The typical titration procedure involves the measured addition of a reactant of known concentration (titrant) into a solution that contains a reactant of unknown concentration (sample) until the reaction fully goes to completion (reaches endpoint). A reaction is said to be complete when one of the reactants (sample) has been fully consumed by the reaction process. Since the total volume of the titrant added to the sample at endpoint may be measured and the stoichiometry of the reaction mechanism is known then is a simple matter to determine the exact quantity of reactant within the titrated sample (i.e. unknown concentration of reactant). The most difficult part of this procedure is determining when the endpoint of the titration actually occurs so that the volume may be measured. In the past this has been done manually introducing human error.

For example, a chemist needs to determine the total acidity of a public drinking water supply. She could perform an acid-base neutralization titration in which she would add a titrant (sodium hydroxide of a known concentration) to known volume of the drinking water sample until the total acidity has been determined. Total acidity in natural waters is defined as acidity that comes from mineral acids, weak organic acids and mostly carbon dioxide, (as carbonic acid). Since the phenolphthalein indicator endpoint pH of 8.3 corresponds to the neutralization of carbonic acid to carbonate, the endpoint is an excellent indication of the total acidity of the water sample. By taking a measurement of the total volume of titrant added to reach endpoint, (when the color of the solution changes from colorless to pink) the chemist is able to determine the exact molar strength of the drinking water sample.

There are titration chemistries that rely on color indicators for endpoint determination. Accurate endpoint determination depends upon a suitable indicator that reflects chemical changes that are occurring in the entire volume of the titrated sample. The current generation of automated titrators are severely limited because these instruments have only the capability of detecting color changes in a small fraction of the total sample volume. Consequently, many titration procedures still require a skilled analyst to interpret the point when the indicator's color change signals the endpoint of the reaction. This introduces much human error into the titration. In fact, there are titration methods that depend on color endpoints (such as dissolved oxygen determination by the azide modification of the Winkler Method) that have not been adapted to titration instrumentation.

Chemists have developed hundreds of different indicators which can be used to determine color endpoints of for all kinds of titration chemistries. For example, to perform water and waste water analysis, acidity can be determined by methyl orange, bromphenol blue and total acidity by phenolphthalein, alkalinity can be determined by a bromcresol green-methyl red mixed indicator, and by phenolphthalein or bromphenol blue, carbon dioxide concentration can be determined with phenolphthalein indicator, iodometric titration methods that use starch as an indicator include: free chlorine, chromate, dissolved oxygen, sulfite and others and chloride concentration can be determined by using diphenylcarbazone as an indicator. There are many other endpoint indicators that range over the entire visible spectrum, from red to blue, that are used to determine the concentration of a constituent or the strength of a solution.

At present there exists a need for a reliable, non-invasive means that will detect the color endpoint for the entire sample volume of a titration automatically and with a high degree of accuracy so that laymen and technicians can perform highly accurate titrations without the expertise of a skilled chemist.

There also exists a need for a titration system which can be altered and customized by the highly skilled chemist or research scientist so that specialized titrations may also be automated.

SUMMARY OF THE INVENTION

The present invention acknowledges and overcomes the aforementioned disadvantages, and addresses the aforementioned needs. Accordingly, it is an object of the present invention to provide a colorimetric titration system designed for fast, high precision, non-invasive determination of concentration of dissolved constituents or determination of solution strength throughout the entire contents of a solution by use of color indicators.

It is another object of the invention to provide for a titration system that can be operated by laymen and technicians without the expertise of a skilled chemist.

It is another object of the invention to provide for a titration system which can be altered and customized by the highly skilled chemist or research scientist so that specialized titrations may also be automated.

It is another object of the invention to provide for a titration system which is controlled through an RS-232 interface by a host computer (examples of host computers include IBM-PC and clones, Apple Macintosh, Sun workstations and others) such that software instructions may allow the titrator to detect the endpoint of a titration.

It is another object of the invention to provide for a titration system which can be customized to perform specialized titrations by altering software instructions which allow the titrator to detect the endpoint of a titration.

It is another object of the invention to provide for a titration system which can receive analog output from other devices (i.e. pH electrodes for acid-base titrations, silver electrodes for argentometric titrations, ion selective electrodes for complexometric titrations, noble metal electrodes for redox titrations, double noble metal electrodes for titrations with polarized electrodes, platinum-platinum electrodes for amperometric titrations, temperature sensors for calorimetric titrations, conductivity probes and others) and perform titrations in response to parameters measured by these devices.

Generally, the invention relates to a device for determining the transmissivity of electromagnetic energy in a predetermined frequency band through a test sample. The invention includes a means for generating an electromagnetic signal, such as light, in the predetermined frequency band and a means for modulating the electromagnetic signal with a second signal of predetermined strength for transmitting the modulated signal through the sample. Additionally, the present invention includes a means for receiving the modulated signal from the sample and a means for demodulating the modulated signal from the receiving means to obtain the second signal. Finally, the invention includes a means for detecting a strength of the second signal from the demodulating means. The present invention also relates to a colorimetric titrator which includes the device for determining the transmissivity of a sample. For example, the means for producing an electromagnetic signal may be an L.E.D which emits radiant energy, or more specifically, light. The means for modulating the electromagnetic signal with a second signal, may be for example, a frequency generator for modulating an intensity of the light or radiant energy at a modulation frequency. The radiant energy is partially absorbed by an adjacent solution within a sample beaker having a color indicator dissolved therein. Radiant energy focusing means focuses the modulated radiant energy transmitted through the sample and beaker on radiant energy detection means. The radiant energy detection means produces a transmitted signal wherein an intensity of the transmitted signal is directly proportional to the intensity of transmitted energy. The demodulating means may include filtering means for filtering the transmitted signal, such that a center frequency of the filtering means matches the modulation frequency of the radiant energy means. The filtering means produces filtered transmitted energy signal representative of only the amount radiant energy transmitted through the solution from the radiant energy source, free of other sources of radiant energy. The colorimetric titrator also includes means for constructing a titration curve, means for computing the first derivative of the titration curve, means for computing the second derivative of the titration curve, control means for controlling titrant addition means in response to the first derivative of the titration curve and means for calling the endpoint of the titration by using the second derivative of the titration curve.

More specifically, the present invention relates to a colorimetric titration system designed for fast, high precision, non-invasive determination of concentration of dissolved constituents or determination of solution strength throughout the entire contents of a solution by use of color indicators. Light from a digitally controlled light source is modulated at a high frequency, 5000 hertz, for example, by a current source. This modulated light passes through a sample in a clear glass beaker and is partially absorbed, depending on the transmissivity of the solution being titrated. The modulated light from the light source and ambient light "noise" from the environment are detected by a radiant energy sensor. Examples of ambient light "noise" are sunlight, light from florescent or incandescent sources (modulating at 120 hertz), shadows cast by passersby, etc. A signal produced by the radiant energy sensor is fed to a bandpass filter where the center frequency of the filter is set to match the light modulation frequency of the radiant energy source. Ambient light and low frequency disturbances such as transient shadows are eliminated in this manner and protection of the sample from ambient light (such as a cover) is obviated, thus increasing ease of operation and usefulness for the end user. Any color indicator can be used, depending of course on the dissolved constituent of interest, ranging the visible spectrum from phenolphthalein red to iodine-starch blue. For example, the dissolved oxygen concentration can be determined by exploiting the dark blue color that is produced by the iodine-starch complex formed by the azide modification of the Winkler method. In this case, a red light source would be used since the blue solution will most readily absorb red light. The solution containing the indicator can then be titrated to a colorless endpoint using the titrator according to the present invention when interfaced with a computer containing appropriate control software. The titrator is connected to a computer through an RS-232 interface which allows the computer to construct and display a titration curve such that the abscissa is the volume of titrant added and the ordinate is the voltage detected by the radiant energy sensor. The change in absorbance of light as the colorless endpoint is approached can readily be detected by the radiant energy sensor. Software also instructs the computer to construct a table comprising voltages sampled, total titrant volume added and the first and second derivatives of the titration curve for each iteration in order to control the pump and call the endpoint of the titration. The radiant energy sensor has a high sensitivity to the change in absorbance of light as the solution progresses from a deeply colored to a colorless appearance during the titration period. The methods used to control the pump during the titration and to call the end point are discussed below The method used to perform the titration and control the titrant pump is as follows. At the beginning of the titration, specifically the first iteration, the host computer instructs a voltage sample to be taken, stores the voltage sample and then instructs the pump to begin by adding initial volume increment on the first cycle. The initial volume increment is also stored in memory during an iteration. For every iteration the voltage sample and total volume added are recorded after each iteration to build a table for constructing the titration curve and the first derivative of the titration curve. On the second iteration, the computer instructs the second voltage sample to be taken representative of transmitted light again after a predetermined period of time to allow mixing after the first increment has been added. The second voltage sample and total volume added to the sample are also stored in memory by the computer. The first derivative of the titration curve is then computed using the present values of voltage and total volume added and the values of voltage and total volume added from the previous iteration, or may be computed by any suitable means. If the first derivative remains close to zero or does not increase (if the voltage signal does not increase), then the computer increases the volume increment for the next pump cycle. On each subsequent iteration, an increased volume increment is added, the voltage taken, and the first derivative computed. This iteration is repeated until the first derivative or slope of the titration curve begins increase. When the first derivative increases the volume increment for the next iteration is then successively decreased on each iteration by some preset increment of volume. Thus, eventually after many iterations, a preset minimum volume increment set within the software instructions may be utilized. This preset minimum volume can be the smallest increment of titrant that can be reliably delivered by the pump for one iteration. By using this pump control method, the endpoint of the titration is not approached too quickly, so that the endpoint may be accurately called as is discussed below. The colorless endpoint is eventually approached when the slope begins to decrease. The minimum volumetric increment may be used as the first derivative becomes zero or very close to zero again. At the point when the first derivative becomes zero or very close to zero and the voltage signal remains high and constant the endpoint of the titration has been reached for the purpose of pump control. When the first derivative becomes zero or remains within preset value of zero a preset number of iterations (as set in the software) are performed using the preset minimum volume increment, assuring that the actual endpoint can be determined with a high degree of accuracy. After this preset number of iterations, the pump is deactivated as per software instructions. At this point the titration is effectively completed for the purpose of pump control and a complete table of data exists in computer memory storage consisting of a sampled voltage signal and total volume added from each iteration along with the first derivative of the titration curve at each iteration. The titration curve and the first derivative may be displayed on the computer screen in real time during the titration or after the titration has been completed.

A method to call the endpoint of the titration for the purpose of accurately determining the total volume of titrant needed to complete the titration reaction (for example, the total volume required to approach the colorless endpoint) is described as follows and shown in the block diagram of FIG. 14. Obviously, this total volume is used to concentration or quantity of the particular reactant or analyte of interest in the sample solution. The second derivative of the titration curve may be used to determine the actual endpoint of the titration. The aforementioned table of values used to construct the titration curve and the first derivative of the titration curve is also used to calculate the second derivative for each iteration (where possible) by any suitable means via software instruction. The first derivative data may also be numerically smoothed by any known means within the software instructions for the purpose creating the second derivative data within the table. Under software instruction, the computer then searches for the most negative peak in the second derivative data. After the most negative peak is detected, the computer under software instruction looks at the second derivative data at each iteration after the most negative peak for the second derivative value in the table closest or equal to zero. The total volume in the table which corresponds to the second derivative closest to zero after the most negative peak indicates the endpoint of the titration. This corresponding titrant volume is used to compute the concentration of the dissolved constituent by known methods. Alternatively, the total volume corresponding to the endpoint may also be found by instructing the computer to search after the most negative second derivative peak in the table for the total volume corresponding to an iteration where the first and second derivatives are both zero or within some preset value from zero. Finally, the endpoint may be called by searching through the table of data for the total volume corresponding to the first occurring first derivative value equal to zero or within some preset value of zero.

In a first embodiment of the inventive colorimetric titrator, the radiant energy sensor is interfaced to a microcontroller that conditions an analog signal representative of light intensity into a digital format for input to a host computer via an RS-232 interface. In this embodiment, a high precision metering pump is digitally interfaced with the microcontroller within the titrator. All titrations are then controlled from the computer through the microcontroller with software instructions which control pumping rate of titrant in response to the digitized light intensity signal received from the microcontroller as discussed above. The software instructions can display the titration curve on the computer screen after the titration or in real time, and transfer any data to memory storage or any standard spread sheet. In addition to the capability of receiving the analog signal input from the light intensity sensor, the titrator is also capable of receiving analog input from other devices which are used to perform titrations (i.e. pH electrodes for acid-base titrations, silver electrodes for argentometric titrations, ion selective electrodes for complexometric titrations, noble metal electrodes for redox titrations, double noble metal electrodes for titrations with polarized electrodes, platinum-platinum electrodes for amperometric titrations, temperature sensors for calorimetric titrations, conductivity probes and others) converting the analog signal to a digital signal within the titrator, interfacing the digital signal representative of pH, temperature, ion concentration or other input with the microcontroller within the titrator, and interfacing this additional digital signal with the host computer via the RS-232 interface in order to control titrant pumping rate. Thus, a pH, thermal or other titration may be performed in a manner similar to the colorimetric titration using the same software and hardware.

In a second embodiment, a colorimetric detection system is connected to a conventional titration device through existing pH probe or other analog inputs. This embodiment consists of radiant energy means, focusing means for focusing light passing through a sample beaker onto a radiant energy sensor, and means to convert light absorption to an analog voltage signal. Since blue, red, and green wavelength radiant energy means are utilized, absorbance over the entire visible light spectrum is achieved. Thus, titration endpoints using any color indicator can be performed using this embodiment of the present invention. In this application, the colorimetric detection system replaces other probes (i.e. pH electrode) and provides an analog output representative of the light intensity impinging on the radiant energy sensor to a conventional titrator. The existing titrator controls the rate of addition of titrant in response to the light intensity signal, records the data received from the detector, and generates the result.

The advantage of computer-based titration is that redundant hardware within the laboratory is eliminated thus reducing cost and making the instrument extremely flexible when compared to other stand alone titration devices. That is, the host computer can support the device with the software instructions and the titration device can be readily adapted to new applications (many different indicators can be accommodated depending on what constituent the user needs to detect in his solution). Also, the user may perform equivalence or inflection point titrations by altering the software instructions. In addition to this, computer control reduces the skill and time needed to perform every day titrations thus further reducing the cost of the titration while providing the most accurate titration possible.

Other advantages of the invention include a long light path length of the titration container (the diameter of the beaker), which results in a higher degree of accuracy and reproducibility than other techniques since other techniques measure parameters in a small fraction of the total sample volume. No sample carry over occurs since the device never comes in contact with the titrant or the solution. Furthermore, large volumes can be easily titrated which means little or no method modification is required to interface with the instrument. Moreover, the inventive titration system can titrate very small volumes thus making it suitable to perform a titration within a test tube. Also, color detection is highly reliable and samples may be processed much faster than with manual titration techniques. Moreover, due to ambient light rejection the progress of a colorimetric titration may be observed directly by the operator. Other objects, features and aspects of the present invention are discussed in greater detail below.

BRIEF DESCRIPTION OF THE DRAWINGS

The disclosure set forth below is complete and enabling to one ordinarily skilled in the art. Furthermore, the best known mode of the invention is fully described.

DETAILED DESCRIPTION OF THE DRAWINGS

Figure 1:
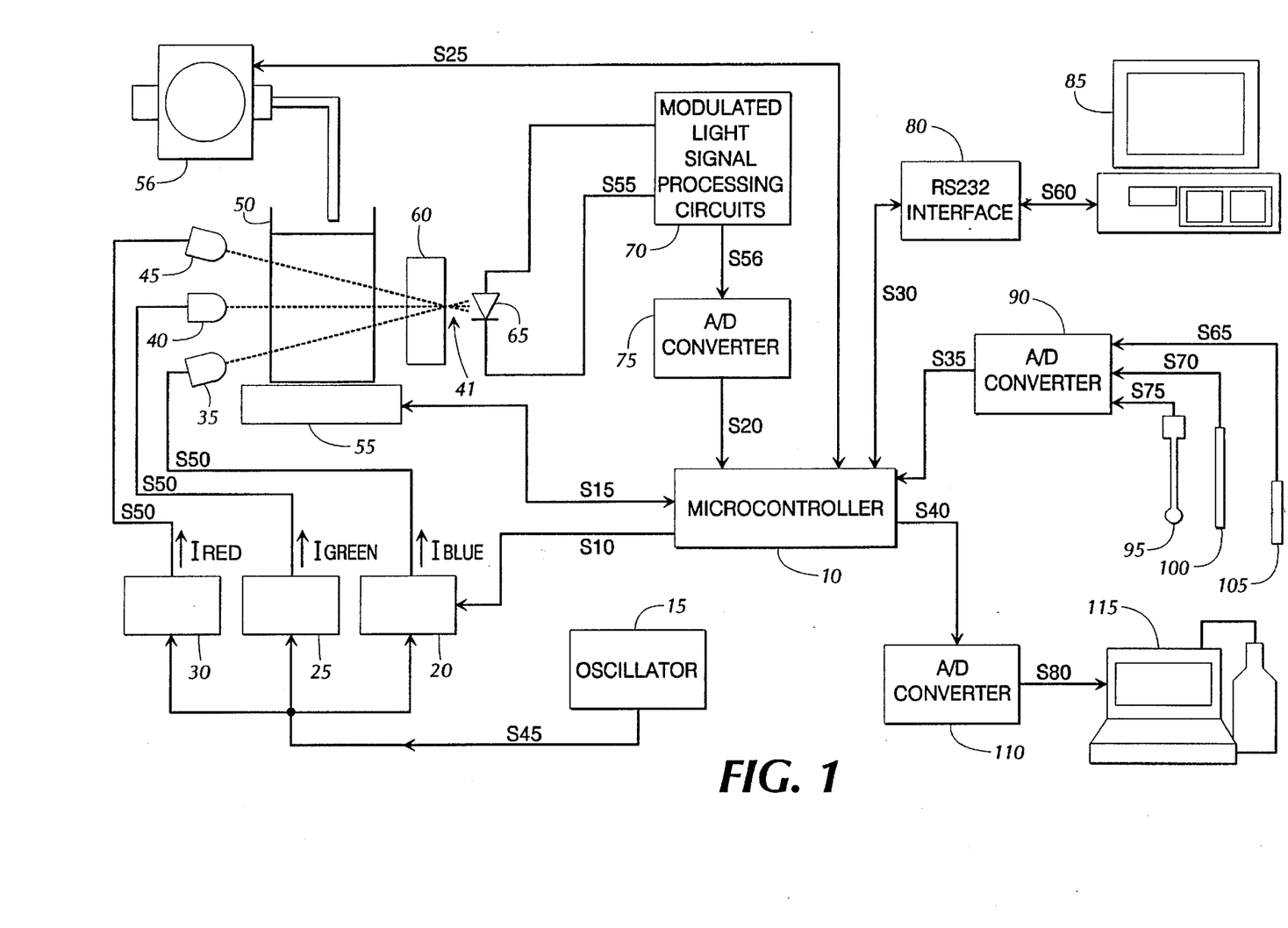
FIG. 1 illustrates a schematic overall layout for the titration system according to the present invention.

Referring to FIG. 1, the titrator unit holds the transparent container 50 within recess 59 (see FIG. 10). Transparent container 50 can be a standard 250 ml beaker, a test tube, or any other container that allows visible light to pass through it. Recess 59 centers the container 50 between light sources 35, 40, and 45 and the cylindrical lens 60. Light sources 35, 40, and 45 are blue, green and red light emitting diodes (LED's), respectively. The two peripheral light sources 35 and 45 are disposed at an angle so as to allow lens 60 to focus each light source a focal point 41 adjacent radiant energy sensor 65. This configuration of angled LED's 35, 45, container 50, and cylindrical lens 65 allows the use of only one sensor 65. Radiant sensor 65 is a photodiode.

Oscillator circuit 15 drives blue, green, and red current sources 20, 25, and 30 respectively. Depending upon the color of an indicator of a solution within transparent container 50, the current source powering the LED which will receive the highest absorbance within the solution is activated. This can be accomplished manually by the user or automatically by the titration system. For manual choice of LED, if a phenolphthalein (pink) indicator is used, the blue current source 20 is chosen by the user and blue LED 35 is powered for this particular titration. On the other hand, if an iodine-starch (blue) indicator is used to determine the amount of dissolved oxygen in the solution, then the red current source 30 that powers red LED 45 is selected. For automatic selection, microcontroller 10 activates each color LED sequentially. While each color LED is turned on, the microcontroller will take a reading and send it to the host computer 85. Host computer 85 will build a titration curve of each color LED and will select the best titration curve for computing the titration endpoint. Additionally, multiple curves can be used to call colorimetric endpoints for titrations that go from one color to another. This feature relieves the user of choosing the proper colored light source for the titration.

The modulated light processing circuits 70 filter output signal S55 from photodiode 65 to remove ambient light, shadow and incandescent light interference. The filtered analog signal S56, which is representative of the intensity of transmitted light impinging upon photodiode 65 from the light sources 35, 40, or 45, is digitized in A/D converter 75 and the resulting digital signal S20 is interfaced with microcontroller 10. Signal S20 is used to control pump 56 and to call the endpoint of the titration, as is discussed in greater detail below.

Host computer 85 communicates with microcontroller 10 via an RS-232 interface 80 via signals S30 and S60. RS-232 interface can be, for example, a Max 232 computer chip from Maxim. The RS-232 interface communicates with the computer via an asynchronous serial port. Host computer 85 communicates with microcontroller 10 to set parameters such as light source choice, current from current sources 20, 25, 30 to control light intensity, control of pump 56, and other titration parameters as will be discussed in further detail below.

Microcontroller 10 also communicates with other analog input devices such as pH electrode 95, ion selective FET 100, temperature probe 105, via signals S75, S80, and S85, respectively, or any other analog input device via an analog to digital signal converter 90 to perform any other titration using a microprocessor algorithm. A/D converter 90 can typically be a 2 channel 16 bit A/D converter such as the AD 7710 module from Analog Devices. A/D converter communicates with microcontroller 10 via signal S35.

Microcontroller 10 sends digital signal S40 representative of titration parameters through a D/A converter 110 to produce analog signal S80. Signal S80 can then be utilized by other titration equipment to determine the endpoint of a titration using the colorimeter of the present invention.

Microcontroller 10 also controls magnetic stirrer 55 via signal S15 and titrant pump 56 via signal S25. Thus, during a titration, microprocessor 10 activates magnetic stirrer 55 while it signals pump 56 to add titrant. Magnetic stirring of the solution during titration assures even distribution of titrant throughout the solution so that the titration endpoint may be determined as accurately as possible.

Figure 2:
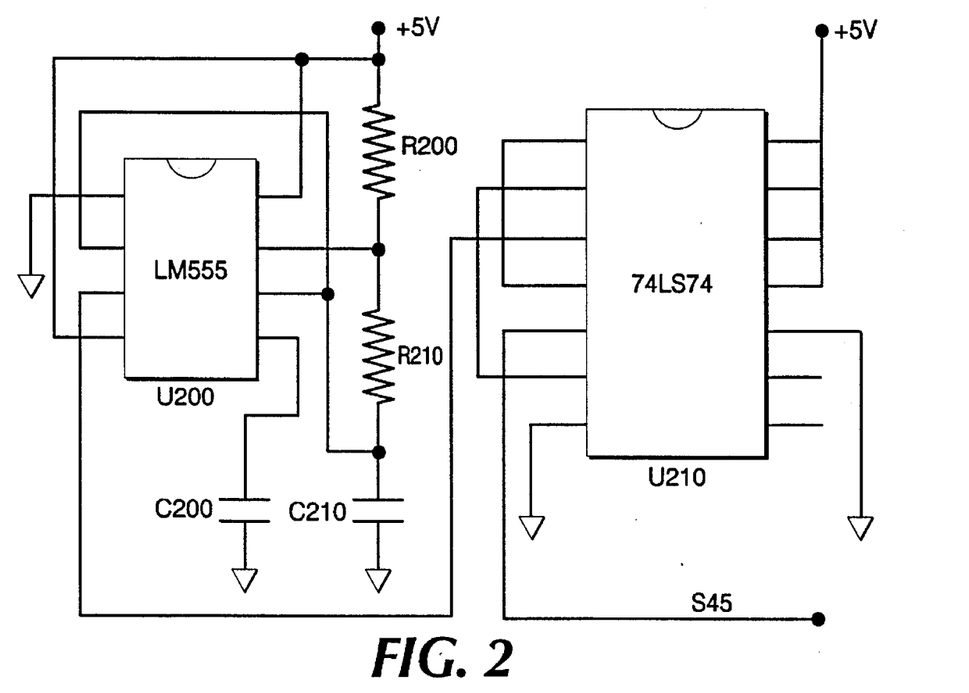
FIG. 2 illustrates oscillator circuitry used in modulating the light signal within the present invention.

FIG. 2 illustrates means for modulating the intensity of radiated energy from the radiant energy sources. More specifically, oscillator circuit 15 in more detail. Integrated circuit chip U200 is used to generate a square wave voltage signal. Signal generation is accomplished by using a quartz crystal oscillator U200 with dividing circuits U210. The output voltage from the integrated circuit oscillator chip U200 is twice the desired modulation frequency of the LED light sources. It also does not have a 50% duty cycle. The divide-by-two portion of the circuit creates a 50% duty cycle output signal and produces a signal output that is half the frequency of the signal from the oscillator chip U200. The total result of the circuit is to produce a signal with the correct modulation frequency and a 50% duty cycle. Resistors R200 and R210 and capacitors C200 and C210 set the oscillation frequency for the oscillator circuit 15. In this case, the frequency is set to 5000 hertz. It should be noted that the ordinarily skilled artisan can use any equivalent circuitry to produce astable oscillators such as one described above by using discrete componentry crystal component oscillators, etc. Also, a variety of modulation frequencies may be chosen.

Figure 3:
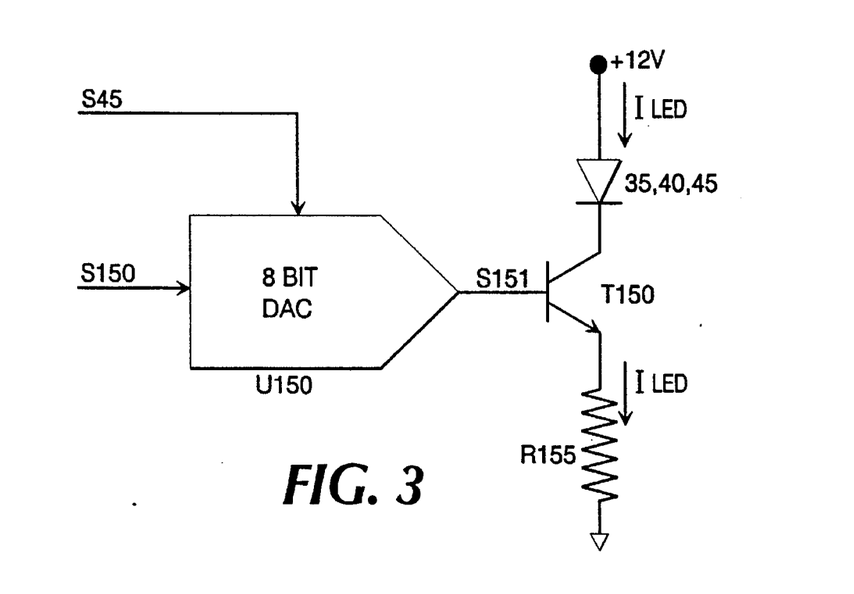
FIG. 3 illustrates the light emitting diode (LED) current source according to the present invention.

FIG. 3 illustrates the LED current sources 20, 25, and 30 in greater detail. Signal s45 from the oscillator is input to D/A converter U150. Additionally, signal S150 which is a digital value from the microcontroller 10 which is input into D/A converter U150 to adjust the amplitude of signal S45. Voltage output from D/A converter U150 is connected to the base of transistor T150. The combination of integrated D/A converter circuit U150, transistor T150, and resistor R155 forms a voltage controlled current source. The current Iled through the LED 45 is given by the equation Iled=((S151−VBE)/(R155). VBE is the transistor base to emitter voltage drop. The amplitude of the current Iled controls the radiant energy flux (or power) from LED 45. It should be noted that other combinations of discrete componentry or discrete componentry and integrated circuits can be utilized to create an equivalent LED current source.

Figure 4:
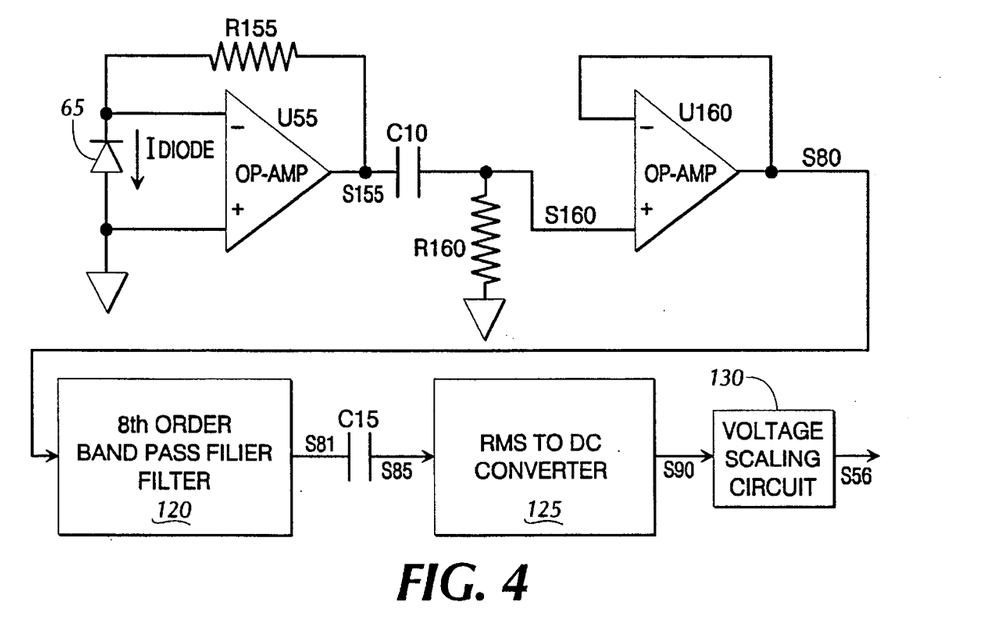
FIG. 4 illustrates the modulating light signal processing circuitry according to the present invention.

FIG. 4 illustrates the modulated light signal processing circuit 70. Reverse current through the photodiode 65 is directly proportional to the radiance of the active surface of the photodiode 65. Op-amp U155 in combination with resistor R155 converts the reverse current through photodiode 65 into an output voltage signal S155. Signal S155 is proportional to the photodiode reverse current and is given by the equation: VS155=(R155)×(Idiode). Capacitor C10 ac-couples output signal S155 thus removing all DC voltages from the signal. This includes the elimination of signals representative of sunlight or offset in the op-amp circuitry, consisting of U155 and R155, to the input of op-amp U160. Resistance R160 is connected between capacitor C10 and the positive input to op-amp U160 and to the electrical ground. The main function of R160 is to provide a bias current for op-amp U160. Op-amp U160 buffers signal S160 from the input of the 8th order bandpass filter 120. This prevents filter 120 from loading the previous function, thus minimizing interaction between functions due to loading.

Figures 9A, 9B:
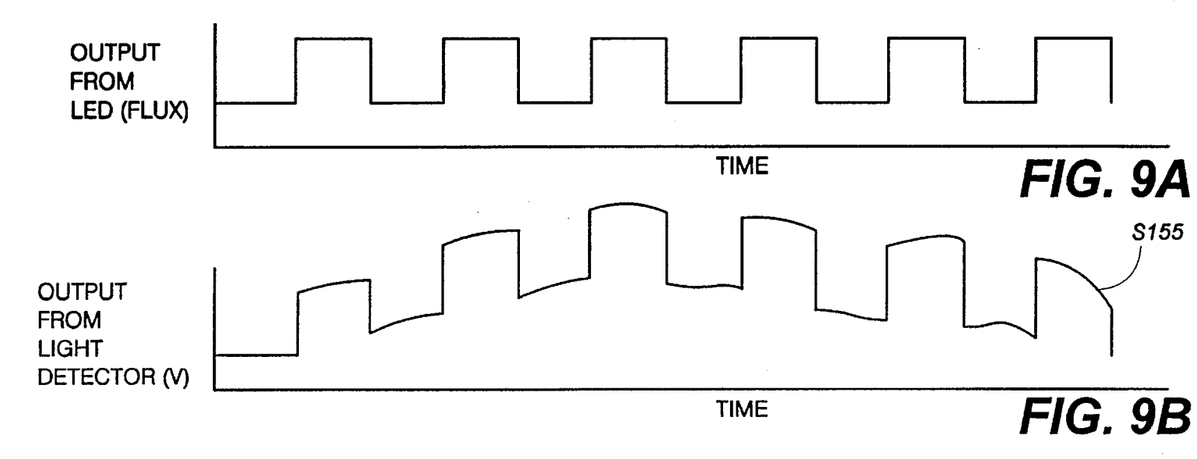
FIGS. 9A–9D illustrates the modulated light signal wave form outputs from the LED, the light detector, the eighth order bandpass filter and from the rms to dc converter.
Figure 9C:
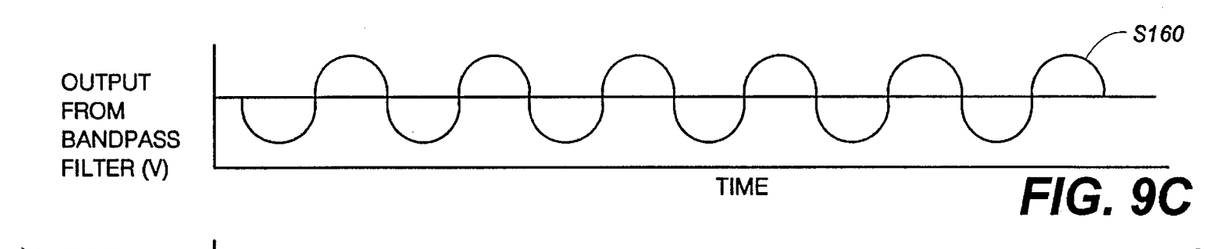
Figure 9D:
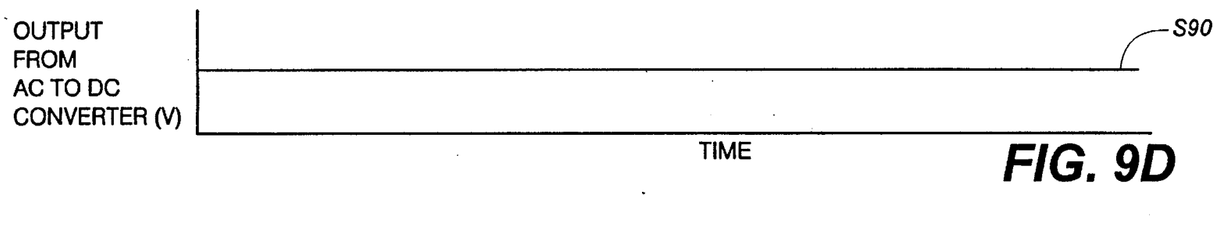

The signal which is produced from photodiode 65 consists of DC very low frequency signals (sunlight and transient shadows), 120 hertz signals from surrounding artificial lighting, and the 5000 hertz amplitude modulated signal from either one or several of LED's 35, 40, and 45, which is proportional to the transmittance of the solution being titrated. Signal S155 represents this combination of signals and is shown in FIG. 9b. Signal S160 has all DC offset removed by the AC coupling effect of capacitance C10. Filter 120 removes all but the 5000 hertz signal transmitted from the LED's 35, 40, and 45, as is shown in FIG. 9c. Signal s81, however consists of the 5000 hertz signal representative of solution transmittance and some DC offset introduced by filter 120 since filter 120 is not ideal. Capacitance C15 AC couples signal S81 to RMS to DC converter 125 thus producing signal S85 which has virtually no DC offset. Signal S85 is then fed to RMS to DC converter 125. Here a DC signal S90 is produced which is equal to the RMS of signal S85. Signal S90 is shown in FIG. 9d. Voltage scaling circuit 130 scales and offsets DC output voltage signal S90 to a value which is useful to other components.

Figure 5:
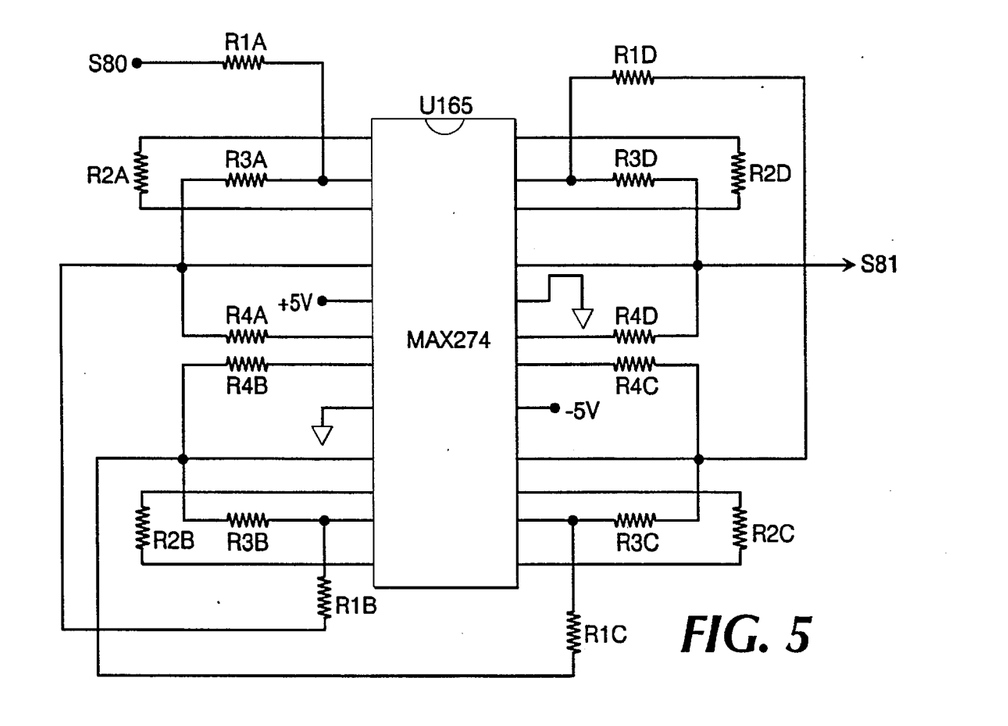
FIG. 5 illustrates an eighth order bandpass filter used within the modulated light signal processing circuity according to the present invention.

FIG. 5 illustrates the eighth order bandpass filter. The bandpass filter consists of four second order analog sections and is of the Butterworth type. The total filter order is eight. The filter can be implemented using discrete active and passive components such as op-amps, resistors and capacitors. Alternatively, the filter can be implemented using an integrated circuit chip and discrete resistors as shown in FIG. 5. The preferred embodiment is that shown in FIG. 5. The integrated circuit chip in FIG. 5 is a MAX274 chip from Maxim, although there are other similar chips available from other manufacturers. It should be noted that the ordinarily skilled artisan can construct an equivalent to filter 120 by using op-amps, capacitors and resistors in such a configuration as to create a state variable filter, or can construct an equivalent filter by other means.

Figure 6:
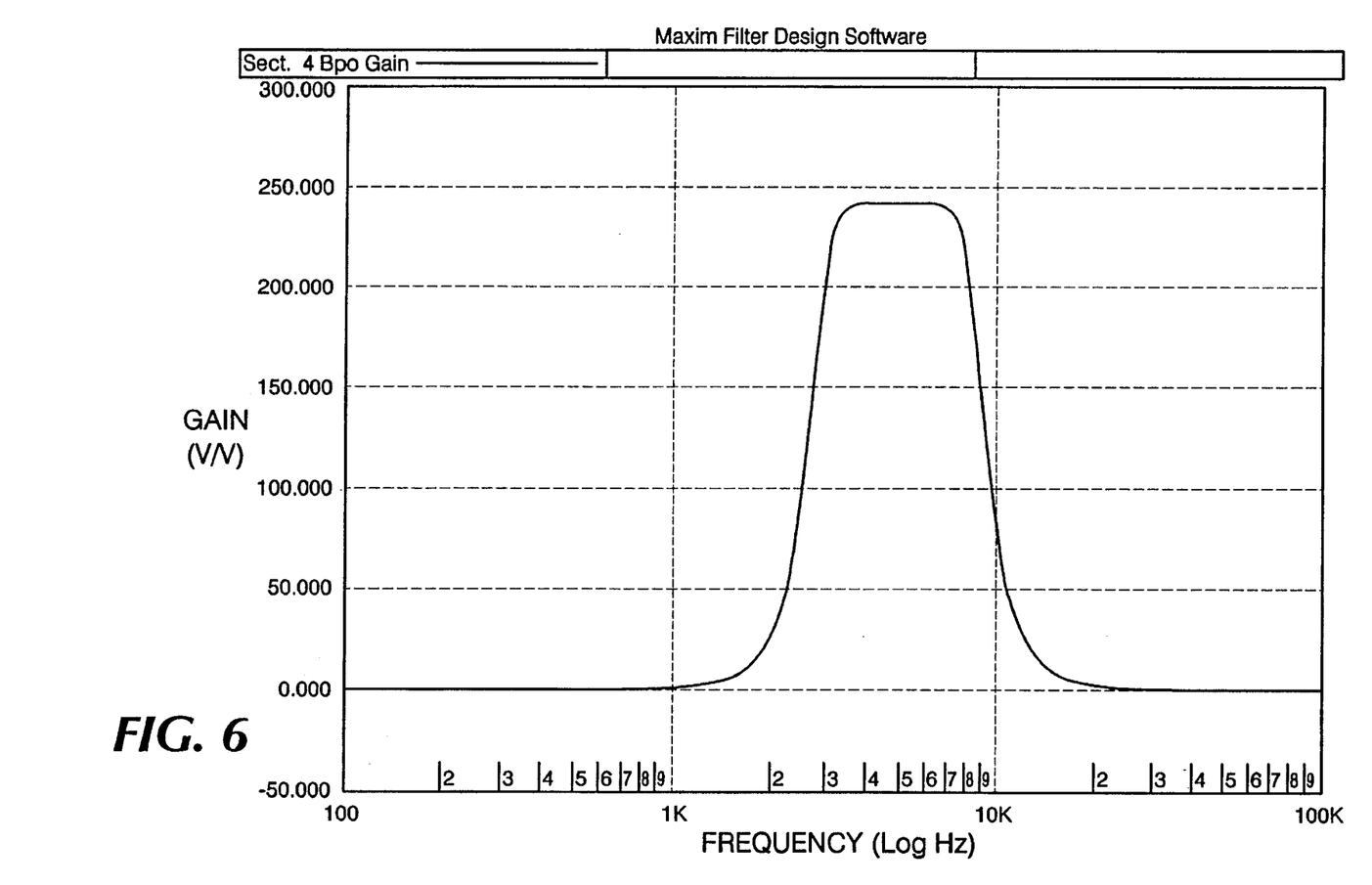
FIG. 6 illustrates a frequency versus signal decibel output for the eighth order bandpass filter.

The gain versus frequency response of the eighth order bandpass filter 120 is shown in FIG. 6. The filter is designed to allow a band of frequencies to pass through the filter with a maximum gain and the rest to be sharply cut off. In the example shown, the pass band varies from 3000 Hz to 7000 Hz. The wide pass band allows for variations in the oscillator output frequency due to temperature changes and component aging without affecting the output amplitude from the filter.

Figure 7:
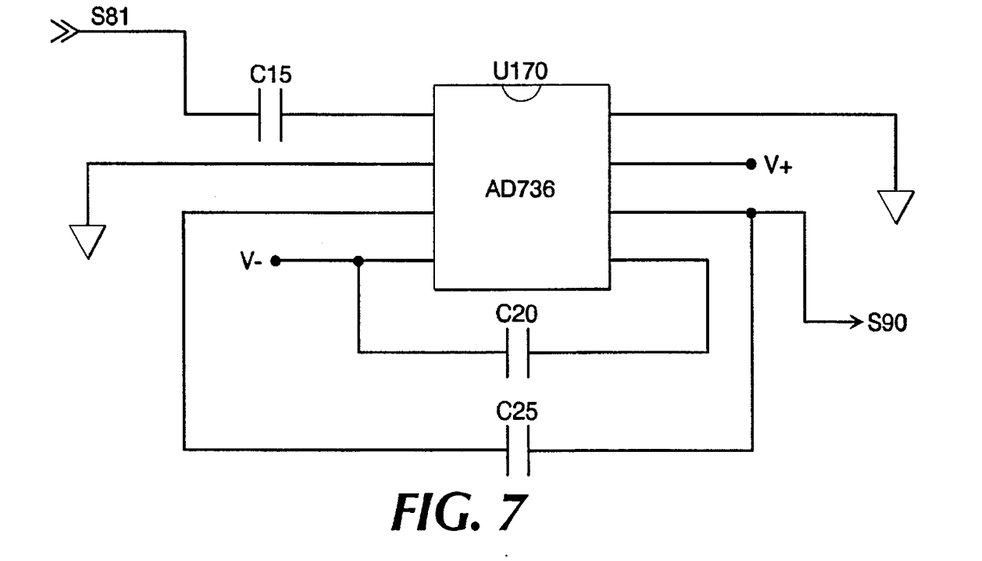
FIG. 7 illustrates a root mean square to direct current converter utilized within the modulated light signal detecting circuitry according to the present invention.

FIG. 7 illustrates the RMS to DC circuitry in more detail. Signal S81 is AC-coupled to microchip U170 through capacitor C15 to eliminate any DC offset in the signal. Capacitors C20 and C25 control the average time from RMS to DC filtering. C20 is the averaging capacitor for the RMS to DC converter. C20 affects both the setting time and the accuracy of the converter and has been chosen in an optimal way for this application. Capacitor C25 provides additional low pass filtering for the converter. This RMS to DC conversion of signal S81 to signal S90 can be achieved by discrete components or by digitization of the sine wave and using software in microcontroller 10 to perform the conversion. However, we believe that the preferred embodiment illustrated in FIG. 7 is the best mode to accomplish this task. DC signal S90 is then scaled by voltage scaling circuit 130, a digital signal s20 produced by A/D converter 75 and then fed to microcontroller 10 for processing.

Figure 8:
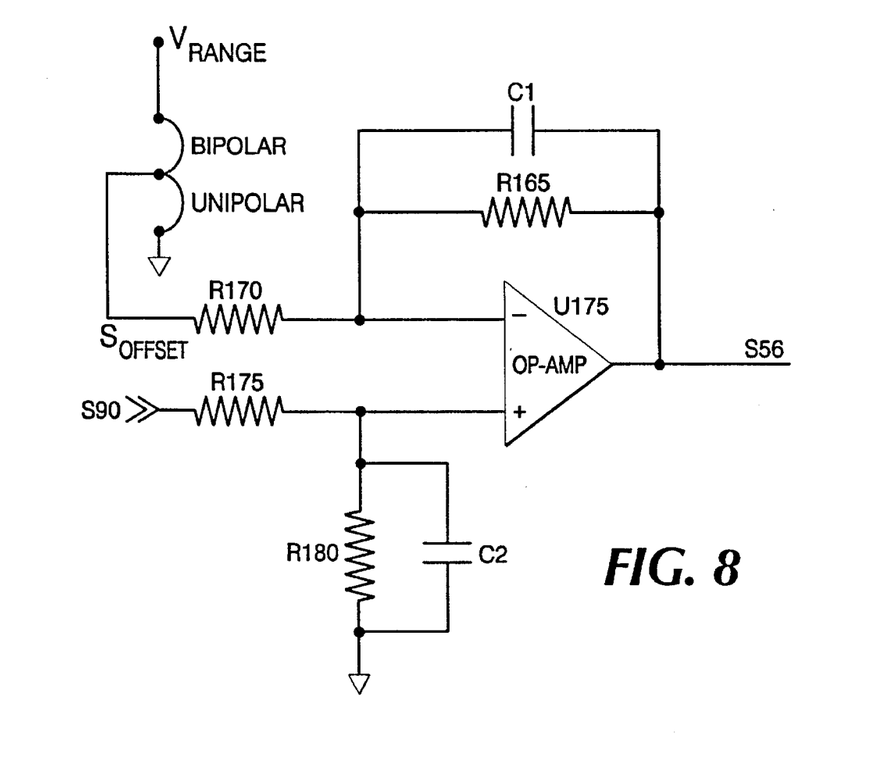
FIG. 8 illustrates a voltage scaling circuit utilized within the modulated light signal detecting circuitry according to the present invention.

FIG. 8 illustrates the voltage scaling circuit. The voltage scaling circuit consists of a differential amplifier with inputs S90 and Soffset and output S56. The differential amplifier is composed of U175, R170, R175, R165, R180, C1, and C2. The voltage scaling circuit provides a gain and an optional offset if the output is desired to be bipolar. The output from the differential amplifier is given by the equation S56= (R165/R170)×(S90−Soffset). An additional constraint of the resistors is that R170=R175 and R165=R180. The capacitors C1 and C2 are used to reduce high frequency noise.

Figure 10A:
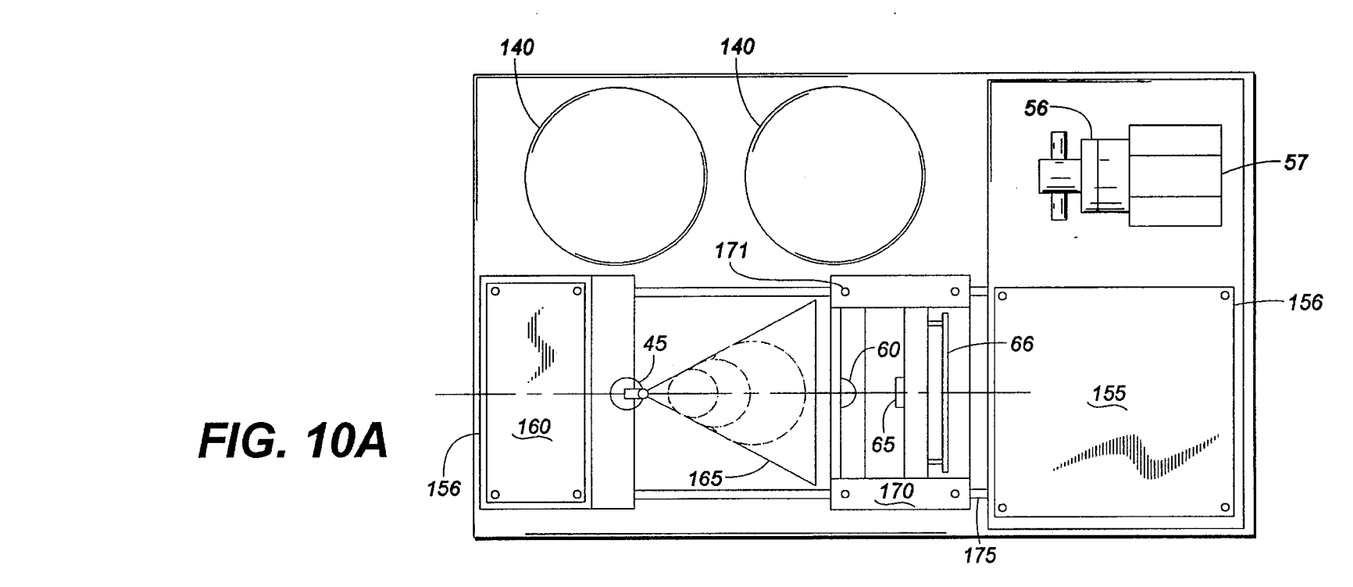
FIGS. 10A and 10B illustrates a mechanical layout of a titrator system according to the present invention.
Figure 10B:
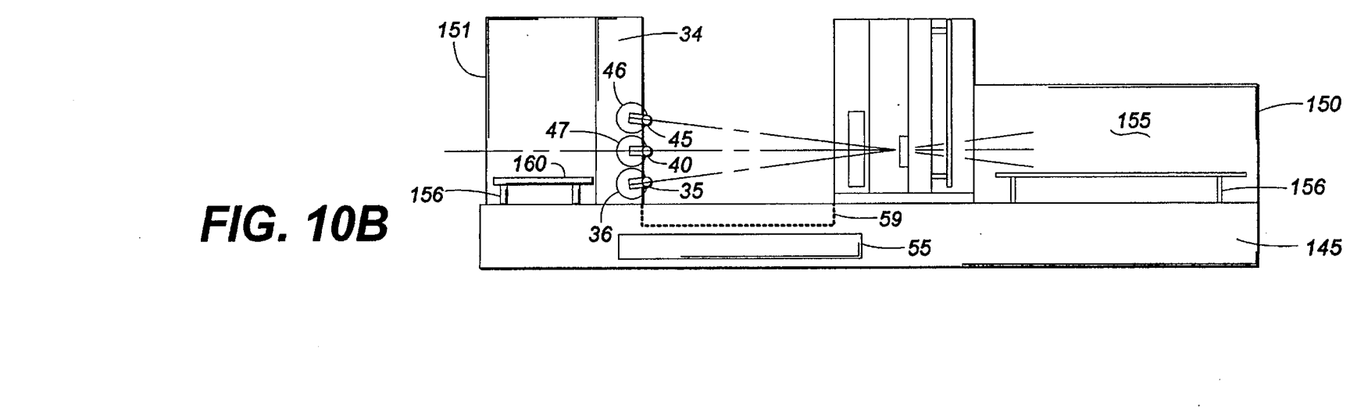

FIG. 10 illustrates the mechanical layout of the titrator. Base 145 holds magnetic stirrer unit 55 under recess 59. LED mount 34 holds LED's 35, 40, and 45 within spheres 36, 41, and 46. LED's are placed into the spheres and then the spheres are press fitted into the LED mount 34. Microcontroller boards 155 and 160 are fastened to base 145 by appropriate fastening means 156. Cover 150 protects and seals microcontroller board 155, titrant pump and stepper motor 57 from chemicals used during titrations. Similarly, cover 151 protects microcontroller board 160 from chemicals used during titration.

The sensor assembly within the titrator is generally indicated as 170. Located on the sensor assembly 170 is cylindrical lens 60, photodiode 65, and associated circuitry 66. Lens assembly 170 slides along track 175 and is secured in place by tightening set screws 171 onto track 170 when the desired position has been reached.

Figure 12A:
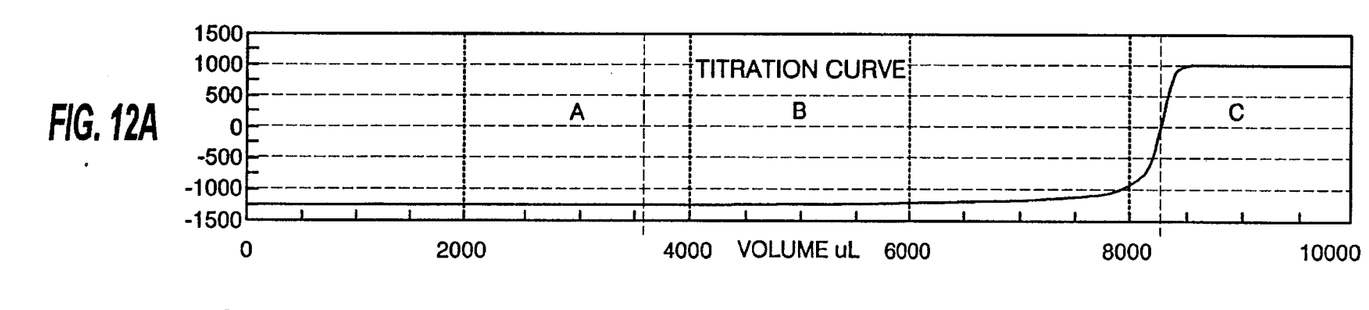
FIGS. 12A–12C illustrates an example of a titration curve computed by the present invention as well as the first and second derivatives of the titration curve.
Figure 12B:
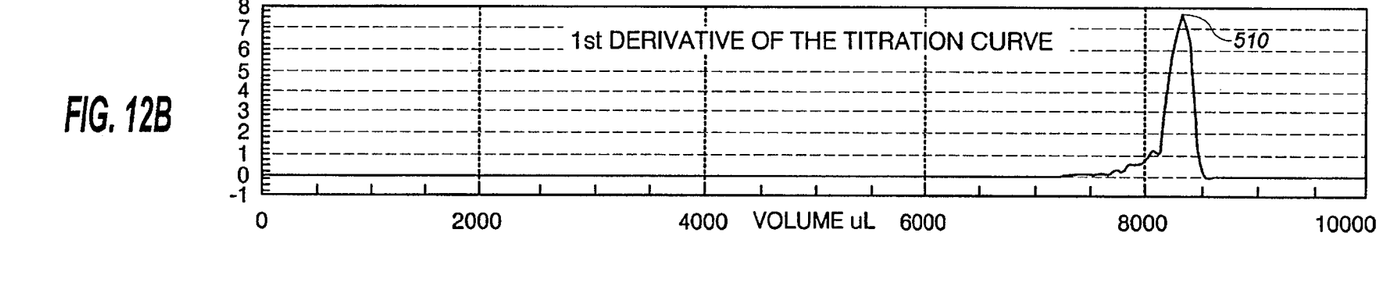
Figure 12C:
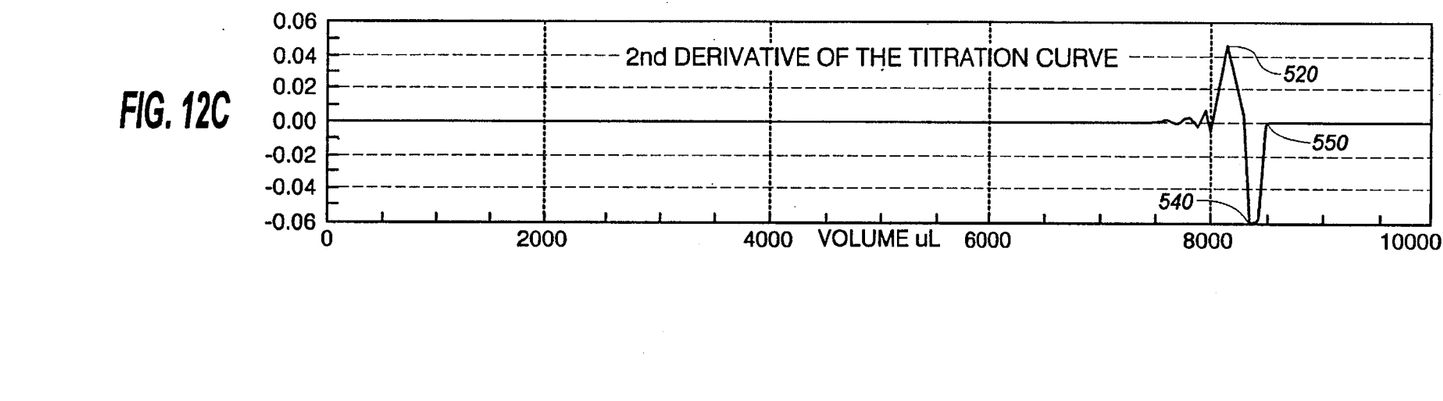
Figure 13:
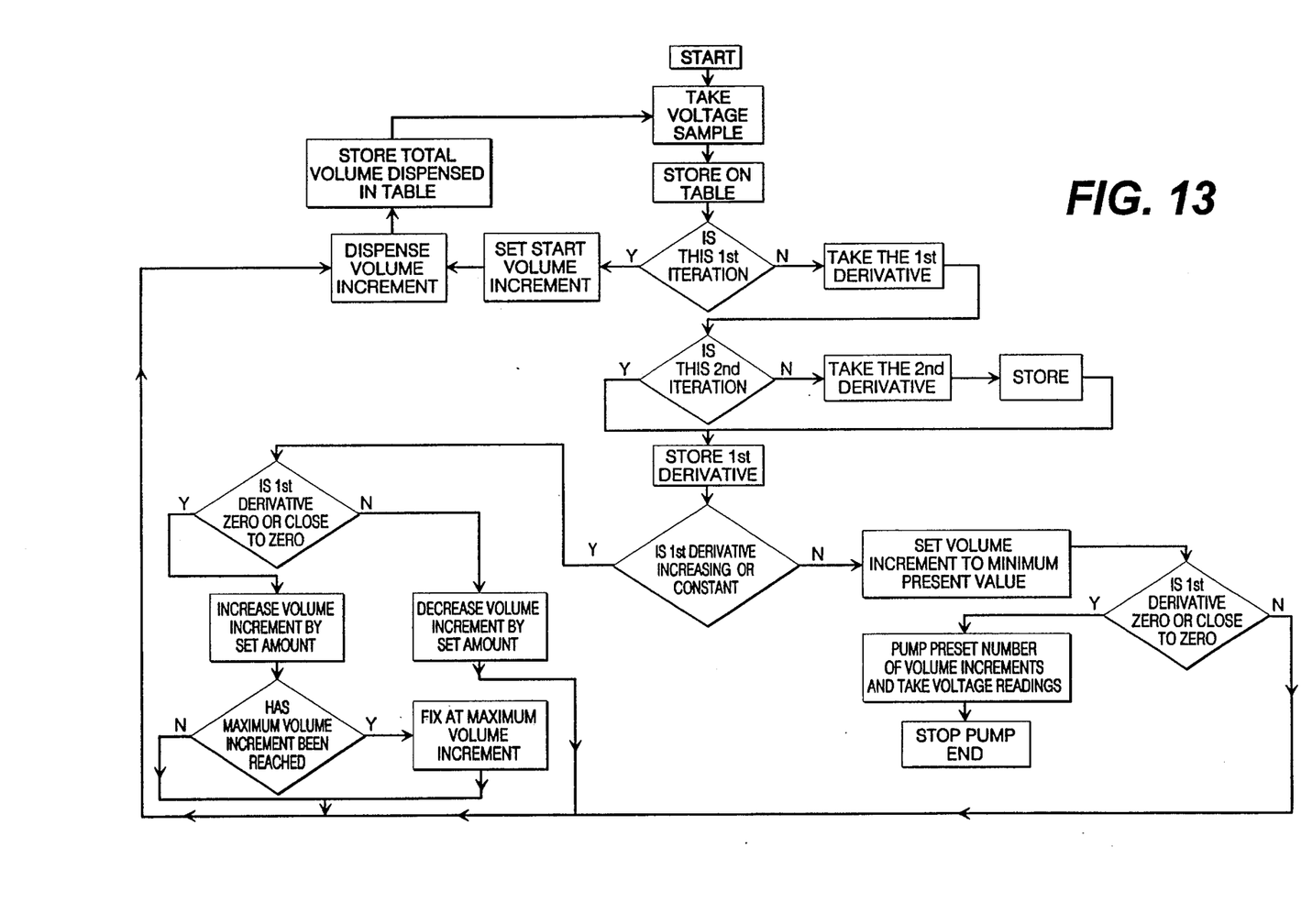
FIG. 13 illustrates a block diagram for titrator control of the pump.
Figure 14:
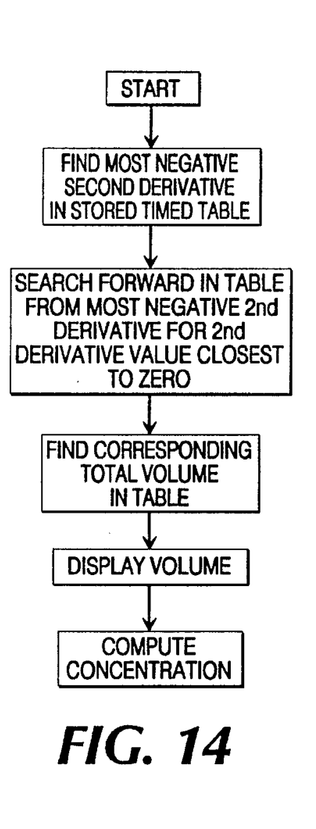
FIG. 14 illustrates a block diagram for computation of the endpoint titrant volume.

The method used to perform the titration and control the titrant pump is shown in FIGS. 12, 13, and 14. At the beginning of the titration, specifically the first iteration as is shown in the block diagram in FIG. 13, the host computer instructs a voltage sample to be taken, stores the voltage sample and then instructs the pump to begin by adding initial volume increment on the first cycle. The initial volume increment is also stored in memory during an iteration. For every iteration the voltage sample and total volume added are recorded after each iteration to build a table for constructing the titration curve and the first derivative of the titration curve. On the second iteration, the computer instructs the second voltage sample to be taken representative of transmitted light again after a predetermined period of time to allow mixing after the first increment has been added. The second voltage sample and total volume added to the sample are also stored in memory by the computer. The first derivative of the titration curve is then computed using the present values of voltage and total volume added and the values of voltage and total volume added from the previous iteration, or may be computed by any suitable means. If the first derivative remains close to zero or does not increase (if the voltage signal does not increase), then the computer increases the volume increment for the next pump cycle. On each subsequent iteration, an increased volume increment is added, the voltage taken, and the first derivative computed. This iteration is repeated in zone A of the titration curve of FIG. 12 until the first derivative or slope of the titration curve begins increase as is indicated in zone B. When the first derivative increases the volume increment for the next iteration is then successively decreased on each iteration by some preset increment of volume. During this period the slope of the titration curve is at a maximum 500 and the first derivative of the peaks at 510, as shown in FIG. 12. Thus, eventually after many iterations, a preset minimum volume increment set within the software instructions may be utilized. This preset minimum volume can be the smallest increment of titrant that can be reliably delivered by the pump for one iteration. By using this pump control method, the endpoint of the titration is not approached too quickly, so that the endpoint may be accurately called as is discussed below. The colorless endpoint is eventually approached when the slope begins to decrease. The minimum volumetric increment is used as the first derivative becomes zero or very close to zero again. At this point, shown as zone C in FIG. 12, as the first derivative becomes zero or very close to zero for a predetermined number of iterations and the voltage signal remains high and constant the endpoint of the titration has been reached for the purpose of pump control. When the first derivative becomes zero or remains within preset value of zero a preset number of iterations (as set in the software) are performed using the preset minimum volume increment, assuring that the actual endpoint can be determined with a high degree of accuracy. After this preset number of iterations, the pump is deactivated as per software instructions. At this point the titration is effectively completed for the purpose of pump control and a complete table of data exists in computer memory storage consisting of a sampled voltage signal and total volume added from each iteration along with the first derivative of the titration curve at each iteration. The titration curve and the first derivative may be displayed on the computer screen in real time during the titration or after the titration has been completed.

A method to call the endpoint of the titration for the purpose of accurately determining the total volume of titrant needed to complete the titration reaction (for example, the total volume required to approach the colorless endpoint) is described as follows and shown in the block diagram of FIG. 14. Obviously, this total volume is used to concentration or quantity of the particular reactant or analyte of interest in the sample solution. The second derivative of the titration curve may be used to determine the actual endpoint of the titration. The aforementioned table of values used to construct the titration curve and the first derivative of the titration curve is also used to calculate the second derivative for each iteration (where possible) by any suitable means via software instruction. The first derivative data may also be numerically smoothed by any known means within the software instructions for the purpose creating the second derivative data within the table. After computation and storage of the second derivative on each iteration, under software instruction the computer then searches for the most negative peak 540 in the second derivative data, as is shown in FIG. 12. There also exists a maximum 520 and one value close to or equal to zero before negative peak 540. After the most negative peak is detected, the computer under software instruction looks at the second derivative data at each iteration after the most negative peak for the second derivative value stored in the table which is closest to zero or equal to zero. This is indicated as point 550 on the second derivative curve of FIG. 12. The total volume in the table which corresponds to the second derivative closest to zero after the most negative peak indicates the endpoint of the titration for the purpose of accurately determining the total volume of titrant needed to complete the titration reaction. Accordingly, this corresponding titrant volume may used to compute the concentration of the dissolved constituent by known methods. Alternatively, the total volume corresponding to the endpoint may also be found by instructing the computer to search after the most negative second derivative peak in the table for the total volume corresponding to an iteration where the first and second derivatives are both zero or within some preset value from zero. Finally, the endpoint may be called by searching through the table of data for the total volume corresponding to the first occurring first derivative value equal to zero or within some preset value of zero.

Figure 11:
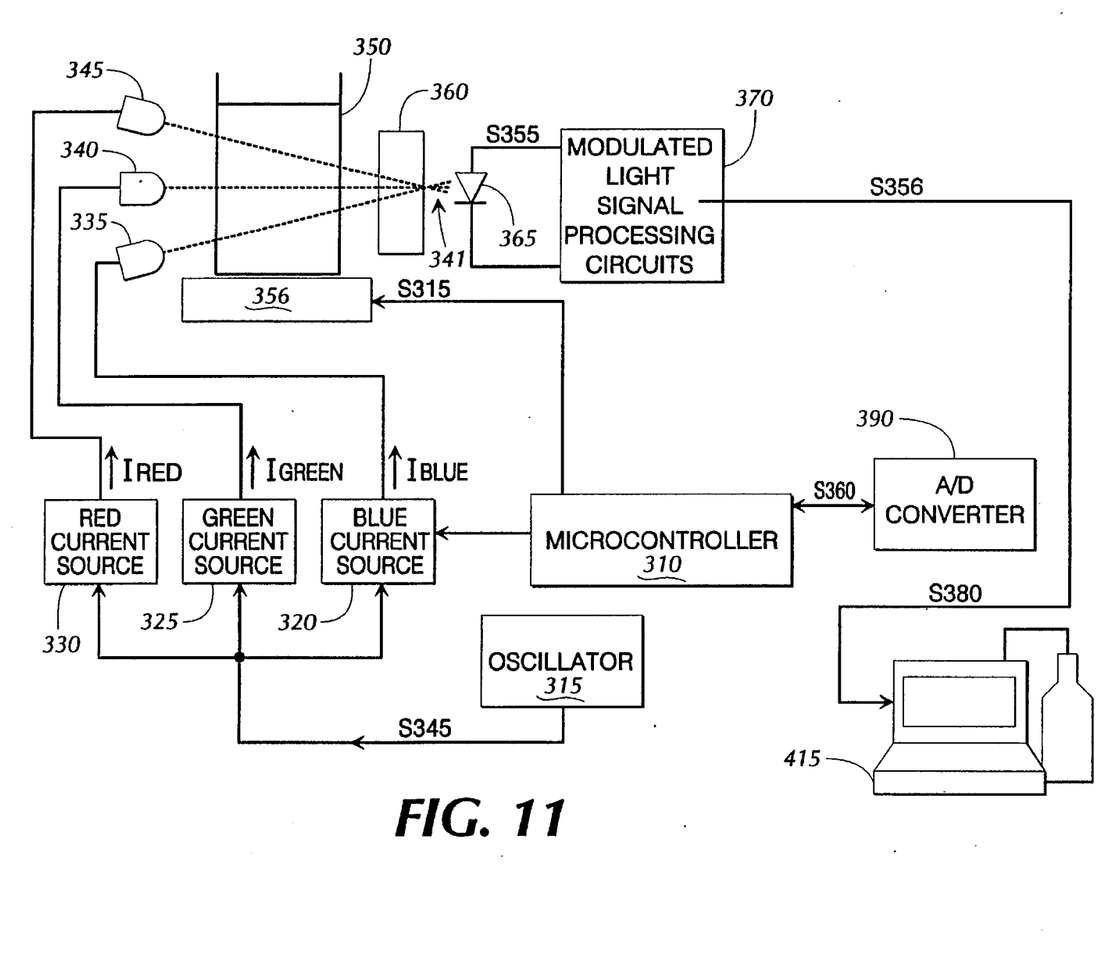
FIG. 11 illustrates a schematic layout of a colorimeter system according to the present invention.

Referring to FIG. 11, in a second embodiment, a colorimetric detection system or colorimeter is connected to a conventional titration device 415 through existing pH probe or other analog inputs. Although the colorimeter is used as a detector, it may have the same mechanical layout as the titrator as disclosed in FIG. 10 without unnecessary components such as a pump, etc. Thus, the colorimeter unit holds the transparent container 350 within recess in a manner similar to the titrator (see FIG. 10). Transparent container 350 can be a standard 250 ml beaker, a test tube, or any other container that allows visible light to pass through it. A recess centers the container 350 between light sources 335, 340, and 345 and the cylindrical lens 360. Light sources 335, 340, and 345 are blue, green and red light emitting diodes (LED's), respectively. The two peripheral light sources 335 and 345 are disposed at an angle so as to allow lens 360 to focus each light source a focal point 341 adjacent radiant energy sensor 65. This configuration of angled LED's 335, 345, container 350, and cylindrical lens 365 allows the use of only one sensor 365. Radiant sensor 365 is a photodiode.

Oscillator circuit 315 drives blue, green, and red current sources 320, 325, and 330 respectively. Oscillator circuit 315 is analogous to the construction of oscillator circuit 15 shown in FIG. 2. Also the construction of the current sources 320, 325, and 330 is analogous to the current sources 20, 25, and 30 shown in FIG. 3. Depending upon the color of an indicator of a solution within transparent container 350, the current source powering the LED which will receive the highest absorbance within the solution is activated through user interface 390. The modulated light processing circuits 370 filter output signal S355 from photodiode 365 to remove ambient light, shadow and incandescent light interference and are analogous to light processing circuitry disclosed in FIGS. 4, 5, and 7. The filtered analog signal S356, which is representative of the intensity of transmitted light impinging upon photodiode 365 from the current sources 335, 340, or 345, can then be utilized by other titration equipment to determine the endpoint of a titration using the colorimeter of the present invention. Microcontroller 310 is analogous to microcontroller 10 as disclosed with the titrator. Additionally microcontroller 310 is interfaced to and controls current sources 335, 340, and 345 in the same way as microcontroller 10 is interfaced to and controls current sources 35, 40, and 45 in the titrator.

Microcontroller 310 also controls magnetic stirrer 355 via signal s315. Thus, during a titration, microprocessor 310 activates magnetic stirrer 355 either automatically or through a user command via user interface 390. Magnetic stirring of the solution during titration assures even distribution of titrant throughout the solution so that the titration endpoint may be determined as accurately as possible by the other titration equipment 415.

In this application, the colorimetric detection system replaces other probes (i.e. pH electrode) and provides an analog output representative of the light intensity impinging on the radiant energy sensor to a conventional titrator. The existing titrator controls the rate of addition of titrant in response to the light intensity signal, records the data received from the detector, and generates the result.

Table I illustrates the discrete components and integrated circuit chips used to practice the invention.

| Component | | Value/Manufacturer |
|---|---|---|
| Resistor | R155 | 100 ohms |
| | R160 | 100 kohms |
| | R165 | 10 kohms |
| | R170 | 10 kohms |
| | R175 | 10 kohms |
| | R180 | 10 kohms |
| | R200 | 1 kohms |
| | R210 | 5 kohms |
| | R1A | 28.7 kohms |
| | R3A | 340 kohms |
| | R2A | 681 kohms |
| | R4B | 532 kohms |
| | R3B | 95.3 kohms |
| | R2B | 523 kohms |
| | R1B | 21.5 kohms |
| | R1C | 13 kohms |
| | R2C | 309 kohms |
| | R3C | 57.6 kohms |
| | R4C | 226 kohms |
| | R1D | 9.76 kohms |
| | R2D | 232 kohms |
| | R3D | 115 kohms |
| | R4D | 226 kohms |
| Capacitor | C1 | 0.1 Microfarad |
| | C2 | 0.1 Microfarad |
| | C10 | 0.1 Microfarad |
| | C15 | 0.1 Microfarad |
| | C20 | 1.0 Microfarad |
| | C25 | 4.7 Microfarad |
| | C200 | 0.043 Microfarad |
| | C210 | 0.01 Microfarad |

-continued

| Component | | Value/Manufacturer |
|---|---|---|
| Transistor | T150 | 2N3904 NPN/National Semiconductor |
| Misc. | U150 | 8 bit Octal Digital to Analog Converter MAX528/Maxim |
| | U155 | OP-80 OpAmp/Analog Devices |
| | U160 | LF351 OpAmp/National Semiconductor |
| | U165 | MAX274 Integrated Circuit/ National Semiconductor |
| | U170 | AD376 RMS to DC Converter/ Analog Devices |
| | U175 | LF351 OpAmp/National Semiconductor |
| | U200 | LM555 Ocillator/National Semiconductor |
| | U210 | 74LS74 Digital Flip Flop/ National Semiconductor |
| Photodiode | 65 | BS500 Sharp Electronics |

It should be understood that various changes to the present invention may be made by the ordinarily skilled artisan, without departing from the spirit and scope of the present invention which is presented in the claims below. Furthermore, it should be abundantly clear that portions of the various embodiments may be interchanged both in whole or in part, including the various components of the overall titrator and the colorimeter system. The ordinarily skilled artisan will understand that this disclosure presents an example of the invention and is not meant to limit the invention presented in the claims in any way whatsoever.

What is claimed is:

1. A device for determining the transmissivity of a sample by passing electromagnetic energy within a predetermined frequency band through the sample, said device comprising:

means located outside of the sample for generating an electromagnetic signal in one predetermined frequency band;

means for modulating said electromagnetic signal with a second signal of predetermined strength for transmitting said modulated signal through the sample;

means located outside of the sample for collecting electromagnetic energy transmitted through the sample, wherein collected electromagnetic energy includes, said modulated signal from the sample and any ambient electromagnetic radiation received by said collecting means;

means for demodulating said modulated signal from said collecting means to obtain said second signal, wherein said second signal substantially represents the amount of said modulated signal received by said collection means after transmission through the sample, and excludes a substantial portion of any ambient electromagnetic radiation received by said collection means; and means for detecting a strength of said second signal from said demodulating means, said strength of said second signal representative of the transmissivity of the sample.

2. The device of claim 1 further comprising:

a pump for adding titrant to the sample.

3. The device of claim 2 further comprising:

a control means for controlling said pump in response to said second signal strength.

4. The device of claim 3 wherein said control means performs the following step of:

sampling and storing a value of said second signal strength at predetermined time intervals.

5. The device of claim 3 wherein said control means performs the following step:

signaling said pump to add a predetermined volume of titrant to the sample for each said time interval.

6. The device of claim 5 wherein said control means performs the step of:

storing a total volume of titrant added to the sample for each time interval.

7. The device of claim 4 wherein said control means performs the additional steps of:

signaling said pump to add a predetermined volume of titrant to the sample for each said time interval; and storing a total volume of titrant added to the sample for each time interval.

8. The device of claim 7 wherein said control means performs the additional step of:

computing a first derivative of said second signal strength with respect to total volume of titrant added to the sample for each time interval.

9. The device of claim 8 wherein said control means performs the additional step of:

deactivating said pump in response to said first derivative.

10. The device of claim 8 wherein said control means performs the additional step of:

adjusting said volume increment of titrant for each time interval in response to said first derivative.

11. The device of claim 8 wherein said control means performs the additional step of:

computing a second derivative of said second signal with respect to total volume of titrant added to the sample for each time interval.

12. The device of claim 11 wherein said control means performs the additional step of:

calculating an endpoint of a titration.

13. The device of claim 11 wherein said control means performs the additional steps of:

storing a value of said first derivative for each said time interval;

storing a value of said second derivative for said each time interval;

searching for a most negative second derivative stored by said control means;

searching forward in time intervals from said most negative second derivative for a second derivative value closest to zero; and indicating a titration end point corresponding to a total volume at a time interval corresponding to said second derivative value closest to zero.

14. The device of claim 1 wherein said electromagnetic signal is the wavelength range of visible light.

15. The device of claim 14 wherein the visible light is substantially red in color.

16. The device of claim 14 wherein the visible light is substantially green in color.

17. The device of claim 14 wherein the visible light is substantially blue in color.

18. The device of claim 1 wherein said electromagnetic signal is generated by a light emitting diode.

19. The device of claim 18 wherein said diode emits blue light.

20. The device of claim 18 wherein said diode emits green light.

21. The device of claim 18 wherein said diode emits red light.

22. An apparatus for measuring the transmissivity of a sample and controlling the addition of titrant to the sample in response to said transmissivity comprising:

light source means located outside of the sample for generating a modulated electromagnetic signal of one predetermined frequency range, said predetermined frequency range selected from a plurality of available frequency ranges, said light source means further comprising:

power source means for providing a power signal;

modulation means for modulating said power signal; and light emission means, responsive to said modulated power signal for emitting said modulated electromagnetic signal, having a known intensity;

light collection means located outside of the sample for collecting electromagnetic energy transmitted through the sample and generating a received electrical signal corresponding to said received electromagnetic energy, said received electromagnetic energy corresponding to said modulated electromagnetic signal and ambient light transmitted through said sample and received by said light collection means;

demodulation means for receiving said received electrical signal and demodulating said received electrical signal to generate a demodulated signal, said demodulated signal corresponding to the amount of said modulated electromagnetic energy transmitted through the sample, substantially excluding any ambient light received at said light collection means; and signal analysis means for determining the transmissivity of the sample based upon the known intensity of said modulated electromagnetic signal and said demodulated signal.

23. The apparatus of claim 22 further comprising:

titrant addition means for adding a controlled amount of titrant to the sample; and control means, responsive to at least said demodulated signal, for controlling said titrant addition means and for varying the rate of addition of titrant to the sample based upon the value of said demodulated signal.

24. The apparatus of claim 22 further comprising:

said light emission means further comprising:

red light emission means for emitting an electromagnetic signal within the red frequency band in response to said modulated power signal;

green light emission means for emitting an electromagnetic signal within the green frequency band in response to said modulated power signal;

blue light emission means for emitting an electromagnetic signal within the blue frequency range in response to said modulated power signal; and control means, responsive to at least said signal analysis means, for selectively providing said modulated power signal to one of said red, green or blue light emission means.

* * * * *